(12) United States Patent
Chowaniec et al.

(10) Patent No.: US 10,542,978 B2
(45) Date of Patent: Jan. 28, 2020

(54) METHOD OF INTERNALLY POTTING OR SEALING A HANDHELD MEDICAL DEVICE

(75) Inventors: Matthew Chowaniec, Middletown, CT (US); Xingrui Chen, Hamden, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 1213 days.

(21) Appl. No.: 13/117,410

(22) Filed: May 27, 2011

(65) Prior Publication Data
US 2012/0303002 A1 Nov. 29, 2012

(51) Int. Cl.
*A61B 17/00* (2006.01)
*A61B 17/072* (2006.01)

(52) U.S. Cl.
CPC .............. *A61B 17/07207* (2013.01)

(58) Field of Classification Search
CPC ........ A61B 17/00017; A61B 17/00115; A61B 17/00128; A61B 17/00398; A61B 17/00734; A61B 17/07207; A61B 17/2927; A61B 2090/0813
USPC .............. 29/527.1–527.4, 611, 841
See application file for complete search history.

(56) References Cited

U.S. PATENT DOCUMENTS

| | | | |
|---|---|---|---|
| 4,155,613 A * | 5/1979 | Brandeau | H01B 11/06 439/90 |
| 4,568,281 A | 2/1986 | Harvey et al. | |
| 4,779,031 A * | 10/1988 | Arends | G05B 19/23 310/58 |
| 5,282,799 A * | 2/1994 | Rydell | 606/48 |
| 5,554,821 A | 9/1996 | Patterson et al. | |
| 6,392,208 B1 * | 5/2002 | Arx | 29/611 |
| 7,722,531 B1 * | 5/2010 | Boche | 600/118 |
| 7,726,863 B2 | 6/2010 | Brandstaetter et al. | |
| 7,812,463 B2 | 10/2010 | Li | |
| 7,845,427 B2 | 12/2010 | Wan et al. | |
| 8,375,572 B2 * | 2/2013 | Lind et al. | 29/841 |
| 8,388,646 B2 * | 3/2013 | Chojin | A61B 18/1445 606/206 |
| 2004/0056538 A1 | 3/2004 | Du et al. | |
| 2006/0255678 A1 | 11/2006 | Du et al. | |
| 2009/0090763 A1 | 4/2009 | Zemlok et al. | |
| 2009/0216229 A1 * | 8/2009 | Chojin | 29/527.2 |
| 2011/0018370 A1 | 1/2011 | Du et al. | |

FOREIGN PATENT DOCUMENTS

| | | |
|---|---|---|
| EP | 0157936 A1 | 10/1985 |
| GB | 1115105 A | 5/1968 |

(Continued)

OTHER PUBLICATIONS

European Search Report for EP 12169440.0-2310 date of completion is Aug. 23, 2012 (9 pages).

(Continued)

*Primary Examiner* — Michael J D Abreu
(74) *Attorney, Agent, or Firm* — Carter, DeLuca & Farrell LLP (57) ABSTRACT

The present disclosure provides a powered surgical instrument including a housing defining an inner cavity therein; at least one internal component disposed within the housing; and potting material injected into the inner cavity encapsulating at least a portion of the at least one internal component.

5 Claims, 5 Drawing Sheets

(56) References Cited

FOREIGN PATENT DOCUMENTS

WO     WO 96/10957 A1     4/1996
WO     WO 2007/002180 A2     1/2007

OTHER PUBLICATIONS

EPO-TEK 377H Technical Data Sheet, Jan. 31, 2007, pp. 1-1, XP55035972, retrieved from the Internet: URL: http://www.epotek.com/sscdocs/datasheets/377h.pdf [retrieved on Jan. 2002], * "graphite filled epoxy", "ESD/EMI shielding of semiconductor devices and electronics".*
Extended European Search Report for appln. No. 16189711.1 dated Feb. 8, 2017.
Anonymous: "Resin dispensing—Wikipedia", Wikipedia, Nov. 6, 2010 (Nov. 6, 2010), pp. 1-6, XP055339617, Wikipedia retrieved from the Internet: URL:https://en.wikipedia.org/w/index.php?title=Resin_dispensing&oldid=395243833#Sealing_of_electronic_parts [retrieved on Jan. 27, 2017] *Chapter 8.1 Sealing of electronic parts*.
Canadian Office Action dated Apr. 25, 2018 issued in corresponding Australian Appln. No. 2,776,740.

\* cited by examiner

METHOD OF INTERNALLY POTTING OR SEALING A HANDHELD MEDICAL DEVICE

BACKGROUND

Technical Field

The present disclosure relates to a powered surgical instrument having housing enclosing a plurality of internal components, including a drive mechanism and a control circuit. More particularly, the present disclosure relates to a surgical instrument including internal components that are encapsulated in a potting material within the housing.

Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose may include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples.

In endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed.

Current known devices can typically require 10-60 pounds of manual hand force to clamp tissue and deploy and form surgical fasteners in tissue which, over repeated use, can cause a surgeon's hand to become fatigued. Gas powered pneumatic staplers which implant surgical fasteners into tissue are known in the art. Certain of these instruments utilize a pressurized gas supply which connects to a trigger mechanism. The trigger mechanism, when depressed, simply releases pressurized gas to implant a fastener into tissue.

Motor-powered surgical staplers are also known in the art. These include powered surgical staplers having motors which activate staple firing mechanisms. However, these motor powered devices also include a variety of internal components (e.g., circuits) which require additional protection from moisture, chemical cleaners, vapors, gases, and biological contaminants. There is a continual need for new and improved powered surgical staplers which provide protection to the internal components.

SUMMARY

The present disclosure provides a powered surgical instrument including a housing defining an inner cavity therein; at least one internal component disposed within the housing; and potting material injected into the inner cavity encapsulating at least a portion of the at least one internal component.

The present disclosure also provides a method for manufacturing a powered surgical device. The method includes injecting a liquid potting material injected into a housing defining an inner cavity therein, the housing including at least one internal component disposed within the housing; and solidifying the potting material to encapsulate at least a portion of the at least one internal component.

The present disclosure further provides a powered surgical instrument. The instrument includes a housing defining an inner cavity therein, the housing including a handle portion; a body portion extending distally from the handle portion; a tool assembly disposed at a distal end of the body portion; a control circuit and a drive motor disposed within the inner cavity, wherein the drive motor is mechanically coupled to the tool assembly and the control circuit is configured to control the operation of the drive motor; and a potting material injected into the inner cavity encapsulating at least a portion of at least one of the control circuit and the drive motor.

BRIEF DESCRIPTION OF THE DRAWINGS

Various embodiments of the subject instrument are described herein with reference to the drawings wherein.

DETAILED DESCRIPTION

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

Figure 1:
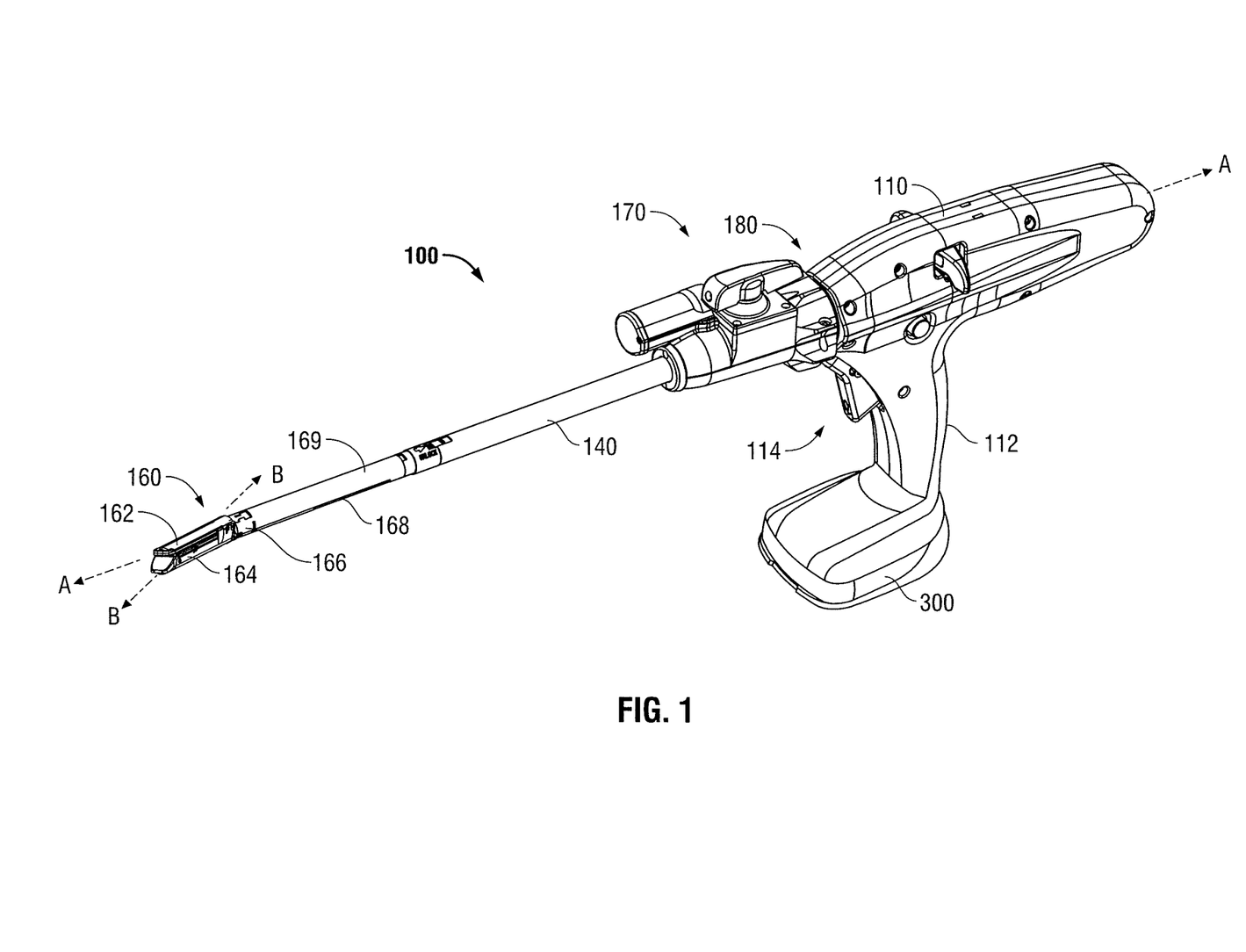
FIG. 1 is a perspective view of a powered surgical instrument according to the present disclosure.

A powered surgical instrument, e.g., a surgical stapler, in accordance with the present disclosure is referred to in the figures as reference numeral 10. Referring initially to FIG. 1, powered surgical instrument 100 includes a housing 110, an endoscopic portion 140 defining a first longitudinal axis A-A extending therethrough, and an articulating tool assembly (e.g., end effector 160), defining a second longitudinal axis B-B extending therethrough. Endoscopic portion 140 extends distally from housing 110 and the end effector 160 is disposed adjacent a distal portion of endoscopic portion 140. In an embodiment, the components of the housing 110 are sealed against infiltration of particulate and/or fluid contamination and help prevent damage of the components by sterilization processes. The instrument 100 also includes a power source 300

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164 to apply linear rows of staples to body tissue either in simultaneous or sequential manner. Either one or both of the anvil assembly 162 and the cartridge assembly 164 are movable in relation to one another between an open position, in which the anvil assembly 162 is spaced from cartridge assembly 164, and an approximated or clamped position, in which the anvil assembly 162 is in juxtaposed alignment with cartridge assembly 164.

It is further envisioned that end effector 160 is attached to a mounting portion 166, which is pivotably attached to a body portion 168. Body portion 168 may be integral with endoscopic portion 140 of powered surgical instrument 100, or may be removably attached to the instrument 100 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may be connectable to endoscopic portion 140 through a bayonet connection. It is envisioned that the loading unit 169 has an articulation link connected to mounting portion 166 of the loading unit 169 and the articulation link is connected to a linkage rod so that the end effector 160 is articulated as the linkage rod is translated in the distal-proximal direction along first longitudinal axis A-A. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, graspers, etc. Such end effectors may be coupled to endoscopic portion 140 of powered surgical instrument 100. An intermediate flexible shaft may be included between handle portion 112 and loading unit. It is envisioned that the incorporation of a flexible shaft may facilitate access to and/or within certain areas of the body.

Figure 2:
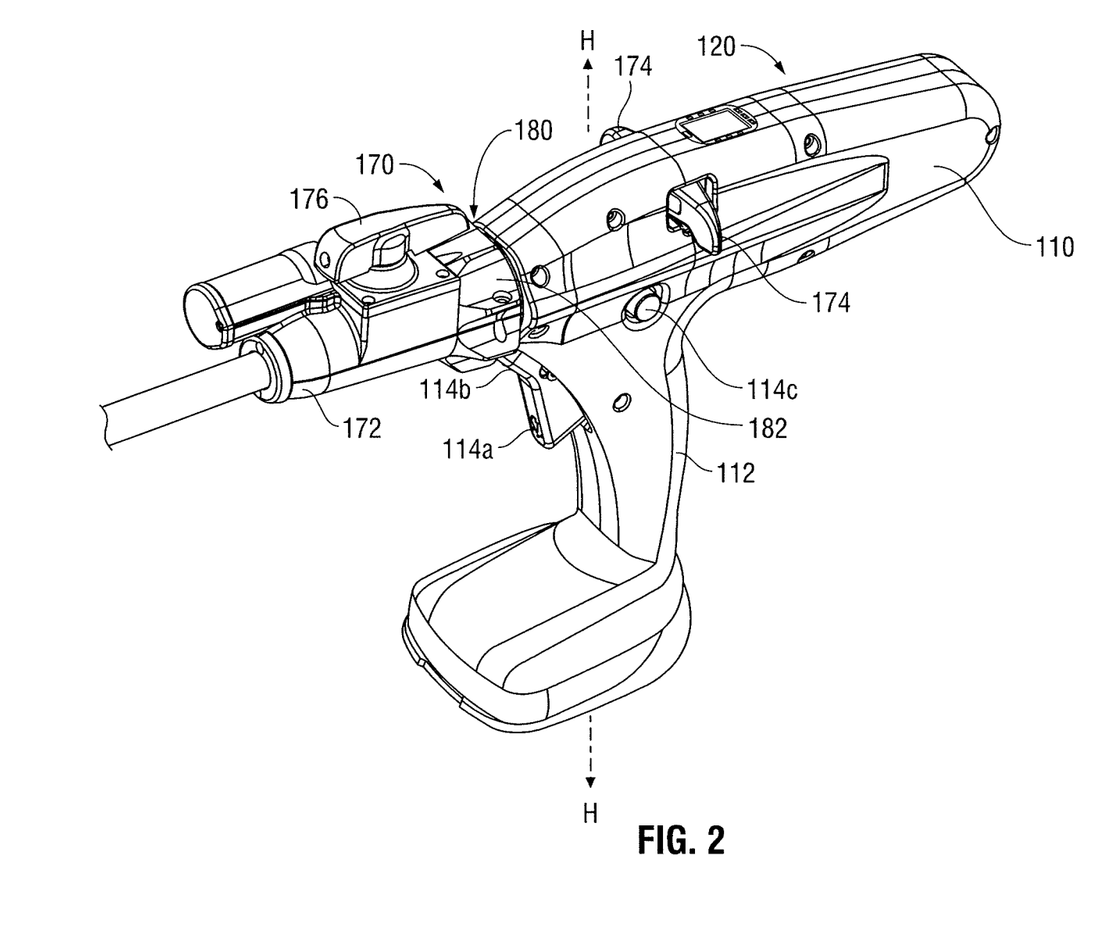
FIG. 2 is a partial enlarged perspective view of the powered surgical instrument according to the embodiment of the present disclosure of FIG. 1 according to the present disclosure.

With reference to FIGS. 1 and 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which helps prevent the handle portion 112 from being squeezed out of the user's hand during operation. Each switch 114a and 114b is shown as being disposed at a suitable location on handle portion 112 to facilitate its depression by a user's finger or fingers.

Figure 4:
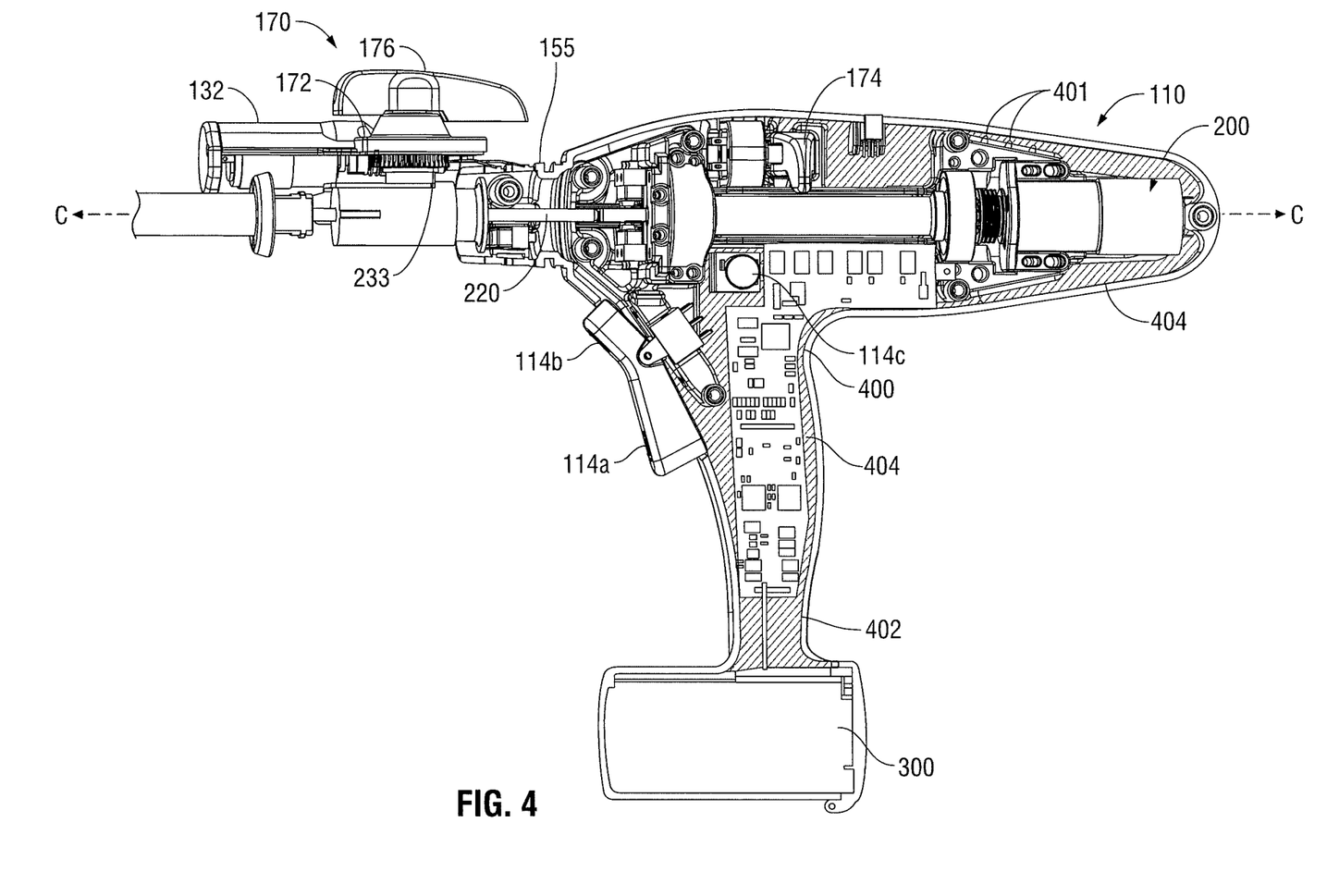
FIG. 4 is a partial perspective sectional view of internal components of the powered surgical instrument of FIG. 1 according to the present disclosure.

Additionally, and with continued reference to FIGS. 1 and 2, switches 114a, 114b may be used for starting and/or stopping movement of a drive mechanism (e.g., drive motor 200) (FIG. 4). The drive motor 200 is configured to actuate the end effector 160, including but not limited to, articulation, closing of the jaw members, ejection of fasteners, cutting, and the like. In one embodiment, the switch 114a is configured to activate the drive motor 200 in a first direction to advance firing rod (not explicitly shown) in a distal direction thereby approximating the anvil and the cartridge assemblies 162 and 164. Conversely, the switch 114b may be configured to retract the firing rod to open the anvil and cartridge assemblies 162 and 164 by activating the drive motor 200 in a reverse direction. The retraction mode initiates a mechanical lock out, preventing further progression of stapling and cutting by the loading unit 169. The toggle has a first position for activating switch 114a, a second position for activating switch 114b, and a neutral position between the first and second positions. Further, the switches 114a and 114b may have high tactile feedback requiring increased pressure for activation.

In one embodiment, the switches 114a and 114b are configured as multi-speed (e.g., two or more), incremental or variable speed switches which control the speed of the drive motor 200 and the firing rod in a non-linear manner. For example, switches 114a, 114b can be pressure-sensitive. This type of control interface allows for gradual increase in the rate of speed of the drive components from a slower and more precise mode to a faster operation. To prevent accidental activation of retraction, the switch 114b may be disconnected electronically until a fail safe switch 114c is pressed.

The switches 114a and 114b are coupled to a non-linear speed control circuit 400 which may include a non-linear speed control circuit implemented as a voltage regulation circuit, a variable resistance circuit, or a microelectronic pulse width modulation circuit. The switches 114a and 144b may interface with the control circuit 400 by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a and 114b to operate the drive motor 200 in multiple speed modes, such as gradually increasing the speed of the drive motor 200 either incrementally or gradually depending on the type of the control circuit being used, based on the depression of the switches 114a and 114b.

Figure 3:
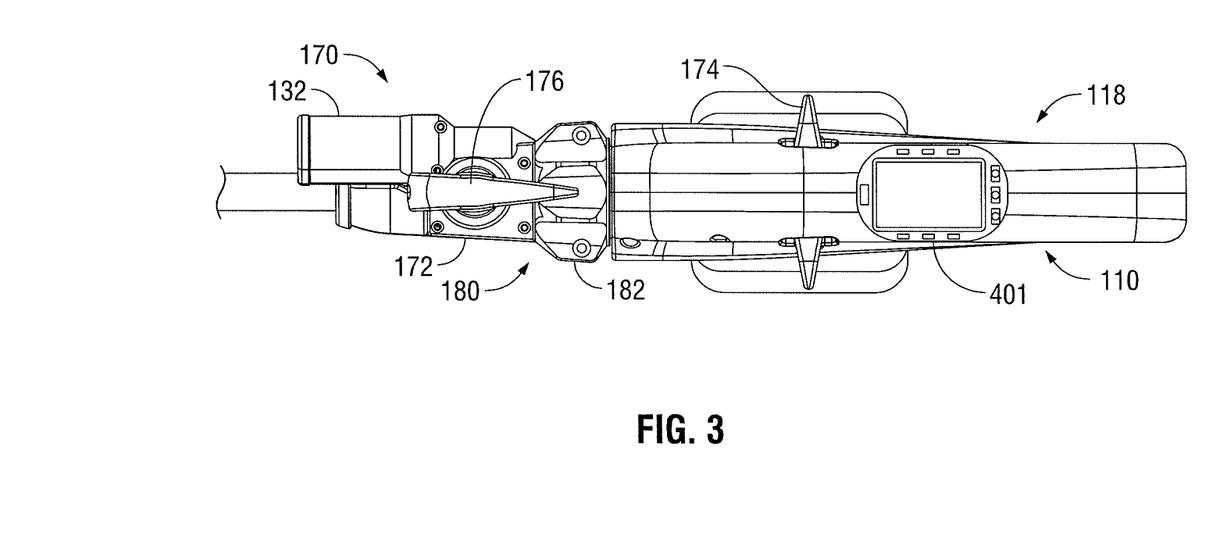
FIG. 3 is a partial enlarged plan view of the powered surgical instrument according to the embodiment of the present disclosure of FIG. 1 according to the present disclosure.

FIGS. 2-4 illustrate an articulation mechanism 170, including an articulation housing 172, a powered articulation switch 174, an articulation motor 132 and a manual articulation knob 176. Translation of the powered articulation switch 174 or pivoting of the manual articulation knob 176 activates the articulation motor 132 which then actuates an articulation gear 233 of the articulation mechanism 170 as shown in FIG. 4. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A. The powered articulation switch 174 may also incorporate similar non-linear speed controls as the clamping mechanism.

Additionally, articulation housing 172 and powered articulation switch 174 are mounted to a rotating housing assembly 180. Rotation of a rotation knob 182 about first longitudinal axis A-A causes housing assembly 180 as well as articulation housing 172 and powered articulation switch 174 to rotate about first longitudinal axis A-A, and thus rotating the end effector 160 about first longitudinal axis A-A. The articulation mechanism 170 is electro-mechanically coupled to one or more conductive rings that are disposed on a housing nose assembly 155 (FIG. 4). The conductive rings may be soldered and/or crimped onto the nose assembly 155 and are in electrical contact with the power source 300 thereby providing electrical power to the articulation mechanism 170. The nose assembly 155 may be modular and may be attached to the housing 110 during assembly to allow for easier soldering and/or crimping of the rings. The articulation mechanism 170 may include one or more brush and/or spring loaded contacts in contact with the conductive rings such that as the housing assembly 180 is rotated along with the articulation housing 172 the articulation mechanism 170 is in continuous contact with the conductive rings thereby receiving electrical power from the power source 300.

Further details of articulation housing 172, powered articulation switch 174, manual articulation knob 176 and providing articulation to end effector 160 are described in detail in commonly-owned U.S. patent application Ser. No. 11/724,733 filed Mar. 15, 2007, the contents of which are hereby incorporated by reference in their entirety. It is envisioned that any combinations of limit switches, proximity sensors (e.g., optical and/or ferromagnetic), linear variable displacement transducers and shaft encoders which may be disposed within housing 110, may be utilized to control and/or record an articulation angle of end effector 160 and/or position of the firing rod 220.

As shown in FIG. 4, the instrument 100 also includes the control circuit 400 electrically coupled to the motor 200 and various sensors disposed in the instrument 100. The sensors detect various operating parameters of the instrument 100 (e.g., linear speed, rotation speed, articulation position, temperature, battery charge, and the like), which are then reported to the control circuit 400. The control circuit 400 may then respond accordingly to the measured operating parameters to control the actuation of the end effector 160 (e.g., adjust the speed of the motor 200, control articulation angle, shut-off the power supply, report error conditions, etc.).

As shown in FIGS. 3 and 4, the control circuit 400 is also coupled to one or more visual devices which may include one or more colored visible lights or light emitting diodes 401 ("LED") to relay feedback to the user. The LEDs 401 may disposed on top of the housing 110 such that the LEDs 401 are raised and protrude in relation to the housing 110 providing for better visibility thereof as shown in FIG. 4. In embodiments, the LEDs 401 may be disposed within the housing 110 as shown in FIG. 4. The LEDs 401 may be activated in a various combinations to denote The multiple lights may be activated in a certain combination to illustrate a specific operational mode to the user. In one embodiment, the LEDs 401 include a plurality of multi-colored lights—a first light (e.g., yellow), a second light (e.g., green) and a third light (e.g., red). The lights are operated in a particular combination associated with a particular operational mode as listed in Table 1 below.

TABLE 1

| Light Combination | | |
|---|---|---|
| Light | Status | Operational Mode |
| First Light | Off | No loading unit 169 or staple cartridge is loaded. |
| Second Light | Off | |
| Third Light | Off | |
| First Light | On | The loading unit 169 and/or staple cartridge are loaded and power is activated, allowing the end effector 160 to clamp as a grasper and articulate. |
| Second Light | Off | |
| Third Light | Off | |
| First Light | Flashing | A used loading unit 169 or staple cartridge is loaded. |
| Second Light | Off | |
| Third Light | Off | |

TABLE 1-continued

| Light Combination | | |
|---|---|---|
| Light | Status | Operational Mode |
| First Light | N/A | Instrument 100 is deactivated and prevented from firing staples or cutting. |
| Second Light | Off | |
| Third Light | N/A | |
| First Light | On | A new loading unit 169 is loaded, the end effector 160 is fully clamped and the instrument 100 is in firing staple and cutting modes. |
| Second Light | On | |
| Third Light | Off | |
| First Light | On | Due to high stapling forces a pulse mode is in effect, providing for a time delay during which tissue is compressed. |
| Second Light | Flashing | |
| Third Light | Off | |
| First Light | N/A | No system errors detected. |
| Second Light | N/A | |
| Third Light | Off | |
| First Light | On | Tissue thickness and/or firing load is too high, this warning can be overridden. |
| Second Light | On | |
| Third Light | On | |
| First Light | N/A | Functional system error is detected, instrument 100 should be replaced. |
| Second Light | N/A | |
| Third Light | Flashing | |

In another embodiment, the LEDs 401 may be multi-colored LEDs which display a particular color associated with the operational modes as discussed above with respect to the first, second and third lights in Table 1.

Figure 5:
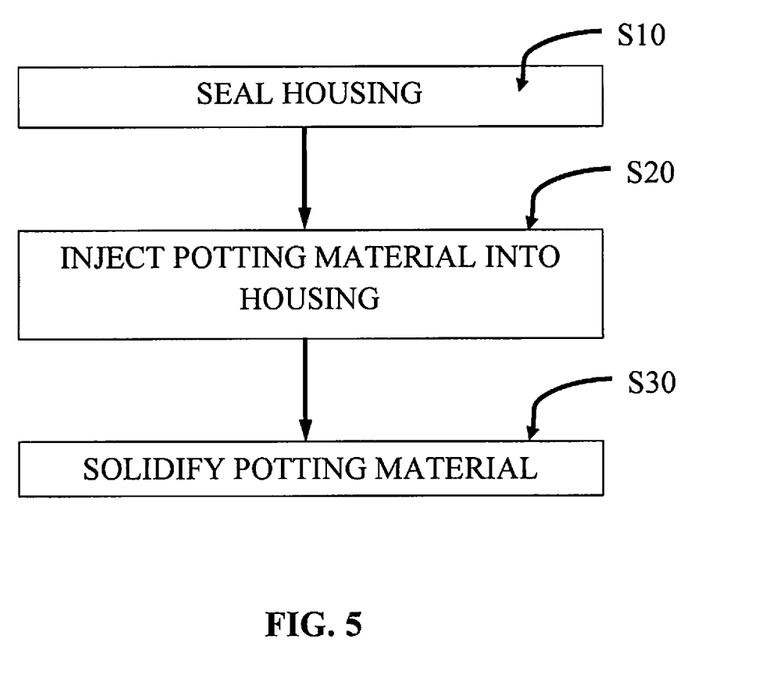
FIG. 5 is a flowchart of an embodiment of a method of injecting potting material according to the present disclosure.

The housing 110 defines an inner cavity 402 in which the control circuit 400 and the motor 200 as well as other components of the instrument 100 are disposed. With reference to FIG. 5, during step S20, a potting material 404 is injected into the cavity 402 so that the material flows into and through the cavity 402, thereby coating and encapsulating the internal components (e.g., the control circuit 400 and the motor 200) of the instrument 100. The material 404 may be injected such that the cavity 402 is either partially or wholly filled with the material 404. Encapsulation of the internal components eliminates voids within the inner cavity 402, which may collect moisture and condensation. Further, the material 404 also seals the components, thereby providing protection from moisture, chemical compounds (e.g., cleaners), vapors, gasses, and biological contaminants. This would also allow for sterilization of the instrument 100 providing for multiple uses.

Prior to injecting the material 404 into the housing 110 during step S20, the housing 110 may be suitably sealed during step S10 to withstand pressures of the sealing process as well as to hermetically seal the housing 110 as described above. The material 404 may be any material that may be any liquid or amorphous material that solidifies upon injection into the cavity 402. In embodiments, the material 404 may be any material or combination of materials (e.g., epoxy) that may change its phase after injection into the housing 110, such that the material 404 is initially in a liquid phase and then transitions into a solid phase to encapsulate the components. Once solidified during step S30, the material 404 may be relatively rigid to protect the components from shock, maintain compliance and to reduce stress under temperature extremes and other environmental conditions.

In embodiments, the material 404 may be a liquid material that may be solidified by one of the following processes which include, but are not limited to, room temperature vulcanization, a thermosetting polymer reaction (e.g., epoxy), curing (e.g., anaerobic or ultra-violet), and combinations thereof. The material 404 may be a polymer, which may include, but not limited to, polyesters, silicones, rubbers, epoxies, nylons, polyphthalamides, liquid crystal polymers, and combinations thereof.

The material 404 once solidified may have a hardness as measured by a durometer from about 5 Shore A to about 100 Shore A, in embodiments from about 10 Shore A to about 50 Shore A. In embodiments, the material 404 may be compliant and/or elastic. This prevents high physical stress that the instrument 100 is subjected to from being transferred to the internal components and/or in embodiments where components or materials of the instrument 100 have discrepant thermal expansion properties. In addition, elasticity of the material 404 absorbs noise and vibration generated by the drive motor 200 and other drive mechanisms, which enhances the handling characteristics of the instrument 100.

The material 404 may include one or more thermally conductive and/or dielectric additives to draw thermal energy from the components as well as to electrically isolate electronic and other sensitive components (e.g., drive mechanisms, batteries, etc.). In addition, material 404 that is thermally conductive also reduces thermal shock and temperature extremes associated with sterilization (e.g., autoclaving) processes. The material 404 may have a thermal conductance from about 0.024 watts per meter·° C. (W/m·° C.) and above. The material 404 may have an electrical resistance from about 3 millivolts per meter under standard temperature and pressure (STP) (mV/m) and above. The material 404 may have a coefficient of thermal expansion from about 1 parts per million/° C. (ppm/° C.) to about 30 ppm/° C., in embodiments from about 5 ppm/° C. to about 20 ppm/° C. The material may have a surface energy from about 10 dynes per centimeter$^2$ (dynes/cm$^2$) to about 45 dynes/cm$^2$, in embodiments from about 20 dynes/cm$^2$ to about 35 dynes/cm$^2$. The term "surface energy" as used herein denotes the disruption of intermolecular bonds that occurs when a surface is created expressed as pressure.

Suitable thermally conductive additives include, but are not limited to, abrasive or lubricious ceramics, boron nitride, aluminum oxide, aluminum nitride, and combinations thereof. The material 404 may include the thermally conductive additive in amount from about 0.5 to about 90% by weight of the material 404, in embodiments, from about 5 to about 25% by weight of the material 404. The material 404 may also be substantially translucent, transparent or combination thereof to allow the LEDs 401 to transmit light therethrough such that the light transmitted by the LEDs 401 is visible to the user.

The material 404 may also include an electro-magnetic shielding additive. Suitable electro-magnetic shielding additives include, but are not limited to metallic compounds, such as ferrous or nickel-based compounds, as well as carbon-based conductive fibers and powders, and combinations thereof. The material 404 may include the electro-magnetically shielding additive in amount from about 0.5 to about 90% by weight of the material 404, in embodiments, from about 5 to about 25% by weight of the material 404.

It will be understood that various modifications may be made to the embodiments shown herein. Therefore, the above description should not be construed as limiting, but merely as exemplifications of preferred embodiments. Although specific features of the powered surgical instrument are shown in some of the drawings and not in others, this is for convenience only as each feature may be combined with any or all of the other features in accordance with the aspects of the present disclosure. Other embodiments will occur to those skilled in the art and are within the following claims.

What is claimed:

1. A method for manufacturing a powered surgical device, the method comprising:
    sealing a housing of the powered surgical device, the housing defining a cavity therein;
    injecting a liquid potting material including an electromagnetic field shielding additive in an amount from about 16% to about 90% by weight of the liquid potting material into the cavity of the sealed housing to hermetically seal the housing, cavity including:
        a motor disposed within the cavity;
        a light emitting diode disposed within the cavity:
        an electrical switch disposed within the cavity that is configured to cause the motor to actuate jaws of an end effector coupled to the housing; and
        at least one additional internal component disposed within the cavity; and
    solidifying the potting material to encapsulate the light emitting diode and at least a portion of the motor, at least a portion of the electrical switch, and at least a portion of the at least one internal component,
    wherein the potting material is substantially transparent.

2. The method according to claim 1, wherein the potting material includes at least one additional additive selected from the group consisting of a thermally conductive additive, a dielectric additive, and combinations thereof.

3. The method according to claim 2, wherein the thermally conductive additive is selected from the group consisting of abrasive ceramics, lubricious ceramics, boron nitride, aluminum oxide, aluminum nitride, and combinations thereof.

4. The method according to claim 1, wherein the potting material is a polymer selected from the group consisting of polyesters, silicones, rubbers, epoxies, nylons, polyphthalamides, liquid crystal polymers, and combinations thereof.

5. The method according to claim 1, wherein the electromagnetic field shielding additive is selected from the group consisting of ferrous compounds, nickel-based compounds, carbon-based conductive fibers, carbon-based conductive particles, and combinations thereof.

* * * * *